United States Patent [19]

Halcourt et al.

[11] 4,220,597
[45] Sep. 2, 1980

[54] PROCESS FOR THE PREPARATION OF ANTHRAQUINONE

[75] Inventors: Kurt Halcourt, Leverkusen; Paul Losacker, Leichlingen; Manfred Martin, Cologne; Norbert Schenk; Wulf Schwerdtel, both of Leverkusen, all of Fed. Rep. of Germany

[73] Assignee: Bayer Aktiengesellschaft, Leverkusen, Fed. Rep. of Germany

[21] Appl. No.: 6,402

[22] Filed: Jan. 25, 1979

Related U.S. Application Data

[63] Continuation of Ser. No. 815,044, Jul. 12, 1977, abandoned.

[30] Foreign Application Priority Data

Jul. 31, 1976 [DE] Fed. Rep. of Germany ....... 2634605

[51] Int. Cl.$^2$ ............................................. C07C 49/68
[52] U.S. Cl. .................................................. 260/369
[58] Field of Search ................................. 260/369, 365

[56] References Cited

U.S. PATENT DOCUMENTS

| | | | |
|---|---|---|---|
| 2,652,408 | 9/1953 | Lecher et al. ........................ | 260/369 |
| 2,938,913 | 5/1960 | Weyker et al. ....................... | 260/369 |

FOREIGN PATENT DOCUMENTS 2460922  7/1975  Fed. Rep. of Germany ........... 260/369

*Primary Examiner*—Patrick Garvin
*Assistant Examiner*—Raymond K. Covington

*Attorney, Agent, or Firm*—Sprung, Felfe, Horn, Lynch & Kramer

[57] ABSTRACT

A process has been found for the preparation of anthraquinone by catalytic oxidation of naphthalene in the gas phase to provide a reaction product, obtained by quenching, cooling or quenching and cooling, containing naphthaquinone and phthalic anhydride, treating said reaction product directly with butadiene to provide tetrahydroanthraquinone, oxidation by means of molecular oxygen to the tetrahydroanthraquinone contained in this reaction product, to give anthraquinone, and separation of naphthalene, phthalic anhydride, anthraquinone and by-products by distillation, the gases produced in the quenching and/or cooling of the gases from the naphthalene oxidation and the gases from the oxidation of the tetrahydroanthraquinone to give anthraquinone being completely or partially recycled to the oxidation of naphthalene, in which a compound with an alkaline reaction is introduced between the reactor in which naphthalene is oxidized and the reactor in which the reaction with butadiene takes place, and/or into the gas streams which are recycled to the oxidation of naphthalene.

The process of the invention reduces considerably the formation of higher-boiling products formed in the continuous preparation of anthraquinone from naphthalene and increases the selectivity of the conversion of naphthalene to anthraquinone. In addition, the process of the invention provides greater freedom in separation of the reaction products since the production of troublesome high-boilers is minimized; and the process results in a reduced formation of carbon dioxide in the oxidation of naphthalene.

8 Claims, No Drawings

PROCESS FOR THE PREPARATION OF ANTHRAQUINONE

This is a continuation of application Ser. No. 815,044, filed July 12, 1977 now abandoned.

The present invention relates to a process for the preparation of anthraquinone from naphthalene.

Processes by which anthraquinone can be prepared from naphthalene are already known. Recent processes for preparing anthraquinone on this basis are described, for example, in Offenlegungsschrift No. 2,218,316 and British Patent Specification No. 1,394,009. The following steps are taken in these processes: (a) catalytic oxidation of naphthalene to give a naphthoquinone, phthalic anhydride and a mixture containing unreacted naphthalene, (b) reaction of the naphthoquinone with butadiene to give tetrahydroanthraquinone, (c) oxidation of the tetrahydroanthraquinone to give anthraquinone and (d) separation of anthraquinone and by-products.

It is known from British Patent Specification No. 1,394,009 that, by cooling the gas stream leaving the reactor for the oxidation of naphthalene, it is possible to obtain a liquid mixture consisting essentially of naphthalene, naphthoquinone and phthalic anhydride, and a gas phase which can consist of nitrogen, carbon dioxide, steam, oxygen and gaseous naphthalene. This gas can be recycled to the conversion of the naphthalene into naphthoquinone and phthalic anhydride, it being necessary to add to this gas the oxygen which is required for the conversion. The liquid mixture consisting of naphthoquinone, phthalic anhydride and naphthalene can subsequently be reacted with butadiene, for example in the liquid phase and under pressure, and the naphthoquinone can thus be converted into tetrahydroanthraquinone. The subsequent oxidation of tetrahydroanthraquinone to give anthraquinone can be carried out using molecular oxygen, for example using a gas which can contain oxygen, nitrogen, carbon dioxide, steam, naphthalene and often also phthalic anhydride, and the exit gas from this oxidation can be recycled to the conversion of the naphthalene into naphthoquinone and phthalic anhydride. Finally, anthraquinone, phthalic anhydride, naphthalene and by-products can be separated, for example by distillation.

It is also known that the gases from the oxidation of naphthalene can be worked up in a cooling stage and a collecting stage and that it is thus possible to obtain a solution consisting essentially of naphthalene, naphthoquinone and phthalic anhydride and an exit gas which can be recycled to the naphthalene oxidation after mixing in the oxygen which has been consumed. In accordance with British Patent Application No. 2975/76 it is possible to work up the gases produced in the oxidation of naphthalene in a quencher and a washer, while maintaining specified conditions, and to obtain a liquid containing naphthalene, naphthoquinone and phthalic anhydride and to obtain, after adding naphthalene, a gas stream which is virtually free from naphthoquinone and phthalic anhydride and which can be recycled to the oxidation of naphthalene.

In accordance with British patent application No. 29726/76 it is possible simultaneously to separate off naphthalene and to carry out the oxidation of the tetrahydroanthraquinone to give anthraquinone, to separate off, by cooling, a part of the organic constituents from the exit gas thus produced and to recycle the remainder of the gas as a feed product to the oxidation of naphthalene.

If the process described immediately above is carried out continously over a prolonged period of time certain quantities of higher-boiling products are obtained when the anthraquinone is worked up. The formation of these products signifies a reduction in the selectivity of the conversion of naphthalene to give anthraquinone.

A process has now been found for the preparation of anthraquinone by catalytic oxidation of naphthalene in the gas phase to provide a reaction product, obtained by quenching and/or cooling, containing naphthaquinone and phthalic anhydride treating said reaction product directly, i.e. without separation of impurities and without the provision of additional solvents, with butadiene to provide tetrahydroanthraquinone, oxidation of said tetrahydroanthraquinone by means of molecular oxygen of the tetrahydroanthraquinone contained in this reaction product, to give anthraquinone, and separation of naphthalene, phthalic anhydride, anthraquinone and by-products by distillation, the gases produced in the quenching and/or cooling of the gases from the naphthalene oxidation and the gases from the oxidation of the tetrahydroanthraquinone to give anthraquinone being completely or partially recycled to the oxidation of naphthalene, in which a compound with an alkaline reaction is introduced between the reactor in which naphthalene is oxidized and the reactor in which the reaction with butadiene takes place, and/or into the gas streams which are recycled to the oxidation of naphthalene.

Provided that volatile or gaseous compounds are used as the compounds with an alkaline reaction, these compounds can be added at one or more points between the reactor in which naphthalene is oxidised and the reactor in which the reaction with butadiene takes place, or into one or more of the gas streams which are recycled to the naphthalene oxidation. For example, volatile or gaseous compounds with an alkaline reaction can be added at the following points: between the reactor in which naphthalene is oxidised and the quenching and/or cooling device, into the quenching and/or cooling device, between the quenching and/or cooling device and the reactor in which the reaction with butadiene takes place, into the reactor in which the reaction with butadiene takes place, into the gases which are recycled from the quenching and/or cooling to the naphthalene oxidation or into the gases which are recycled to the naphthalene oxidation from the oxidation of tetrahydroanthraquinone to give anthraquinone. If nonvolatile compounds with an alkaline reaction are used, it is appropriate to add the latter at points at which a liquid product is present, is conveyed or is formed immediately after the addition of the compound with an alkaline reaction. For example, non-volatile compounds with an alkaline reaction can be added at the following points: shortly before or at the entry of the gases from the naphthalene oxidation into the quenching and/or cooling device, into the quenching and/or cooling device, between the quenching and/or cooling device and the reactor in which the reaction with butadiene takes place, or into the reactor in which the reaction with butadiene takes place.

It is preferable to add the compounds with an alkaline reaction shortly before or at the entry of the gases from the naphthalene oxidation into the quenching and/or cooling device, or to the liquid phase in the quenching and/or cooling device. If a quenching device is used, it is preferentially possible to introduce the compounds with an alkaline reaction into the sump of the quencher or into the circulation of the quencher. If a multi-stage quenching and/or cooling device is used, it is advantageous to introduce the compounds with an alkaline reaction into the first stage of the quenching and/or cooling device.

It is possible to introduce compounds with an alkaline reaction at one or more points. It is advantageous if arrangements are made for the compounds with an alkaline reaction which are introduced to be distributed finely in the particular gas or liquid stream.

The most diverse compounds with an alkaline reaction can be employed within the scope of the process according to the invention. Thus, for example, inorganic and organic compounds with an alkaline reaction can be used. For example, alkali metal and/or alkaline earth metal compounds, ammonia and/or organic bases, for example basic organic nitrogen compounds, can be used. Alkali metal and/or alkaline earth metal compounds which should be mentioned are oxides, hydroxides, carbonates, bicarbonates and salts of organic acids, in particular sodium hydroxide, sodium oxide, sodium carbonate, sodium acetate, sodium oxalate, sodium phthalate, potassium hydroxide, potassium oxide, potassium bicarbonate, potassium acetate, potassium oxalate, potassium phthalate, lithium oxide, lithium hydroxide, lithium carbonate, lithium acetate, calcium hydroxide, calcium carbonate, calcium acetate, calcium maleate, barium oxide, barium hydroxide, barium phthalate and barium oxalate. Organic bases which should be mentioned are primary, secondary and tertiary amines, as well as aromatic and cyclic amines, in particular methylamine, butylamine, diethylamine, isobutylamine, ethylpropylamine, cyclohexylamine, aniline, pyridine, piperidine, quinoline, pyrrole and imidazole.

It is preferable to employ sodium hydroxide, potassium hydroxide, calcium carbonate or ammonia in the process according to the invention.

In each case one or more compounds with an alkaline reaction can be employed. If several alkaline compounds are employed, they can be added at the same point or at different points.

The compounds with an alkaline reaction are added in a gaseous, liquid and/or solid form. It is possible to add the compounds with an alkaline reaction in a pure form or mixed with solvents or diluents. Solvents or diluents which can be used are those which are completely or partially miscible, or immiscible, with the product into which the compounds with an alkaline reaction are introduced. Dilute or concentrated aqueous solutions of sodium hydroxide, potassium hydroxide or ammonia are preferably used. It is also possible to use, for example, mixtures of sodium phthalate and phthalic anhydride or suspensions of sodium carbonate, potassium carbonate or calcium carbonate in naphthalene.

In general, it is completely adequate if the compounds with an alkaline reaction are added in small quantities. The compounds with an alkaline reaction can, for example, be added in an amount of 0.001 to 0.1% by weight, preferably in an amount of 0.005 to 0.01% by weight relative to the naphthalene converted in the naphthalene oxidation.

By means of the process according to the invention it is possible to reduce considerably the formation of higher-boiling products in the continuous preparation of anthraquinone from naphthalene and thus to increase the selectivity of the conversion of naphthalene to anthraquinone. Furthermore, the separation of the reaction products can be carried out with greater freedom from problems, since troublesome high-boilers are produced in a smaller quantity. In addition, the process according to the invention reduces the formation of carbon dioxide in the oxidation of naphthalene.

Anthraquinone can be used as the starting material for the preparation of dyestuffs (see, for example Ullmann's Enzyklopädie der Technischen Chemie ("Encyclopaedia of Industrial Chemistry"), volume 3, page 362 et seq., 3rd edition 1953). The phthalic anhydride which is formed as a by-product can be used as the starting material for the preparation of plasticisers and many other chemical syntheses (see, for example, Ullmann's Enzyklopädie der Technischen Chemie ("Encyclopaedia of Industrial Chemistry"), volume 18, page 556 et seq., 3rd edition 1967).

EXAMPLE 1

The oxidation of naphthalene to give naphthoquinone by means of molecular oxygen is carried out in the gas phase in a multi-tube reactor of conventional construction, which is cooled by means of a salt melt via a secondary cooling circuit. The reactor contains 48 tubes in parallel, each of which has a length of 6 m and an internal diameter of 32.8 mm. Each of the tubes is filled to a height of 3.5 m with catalyst. This gives a total catalyst volume of 145 l. The catalyst consists essentially of vanadium pentoxide, silica and potassium sulfates. The pressure at the inlet of the reactor is 6 bars and the temperature of the salt melt is 330° C. 300 Standard cubic meters per hour of a gas stream which contains 3% by volume of naphthalene, 6% by volume of oxygen and 7% by volume of steam are passed over the catalyst. As well as these components, above all nitrogen and carbon dioxide are present, together with minor quantities of carbon monoxide and other gaseous constituents.

The reaction gases are cooled to 280° C. in a tube cooler (evaporative cooling) and are subsequently brought into contact with liquid reaction product in a quench system. In this the gaseous products are passed in countercurrent to the liquid reaction products. The sump temperature of the quencher is 120° C. and the circulation of the liquid reaction product to the head of the quencher is passed through a cooler. Before being recycled to the oxidation reactor, the gases are subjected to a wash with fresh naphthalene in order to remove reaction products which are present in accordance with their partial pressures. The gases emerging at the head of the washer contain approximately 3% by volume of oxygen and 0.5% by volume of naphthalene and are recycled to the reactor via a blower. In order to dehydrogenate the tetrahydroanthraquinone, part of this gas stream is introduced into the reaction stage scheduled for this purpose and it leaves this reaction section via the head of the column located in this reaction section. The combined gas streams are fed to a naphthalene vaporiser and are brought to a naphthaline content of 3% by volume.

Fresh naphthalene is added into the quenching and/or washing system in an amount of 17 kg per hour. This amount of naphthalene corresponds to the amount of naphthalene which is converted in the oxidation of naphthalene.

The oxygen which is consumed is introduced into the system in the form of air, and, by suitable admixture of air to the circulation gas, the oxygen content in the oxy-dehydrogenation stage of tetrahydroanthraquinone to give anthraquinone is approximately 4% by volume. The fraction of entrained inerts, above all nitrogen, and of gaseous by-products formed, above all steam, carbon dioxide and carbon monoxide, is withdrawn from the two combined gas circuits. This is achieved by taking off a corresponding purge stream, which is removed from the process.

The condensed liquid reaction products are withdrawn jointly from the quenching system. The quantity is 70 kg/hour, containing about 10% by weight of naphthoquinone, 8% by weight of phthalic anhydride and unreacted naphthalene. 5 mol % of the naphthalene reacted are converted into carbon dioxide during this reaction stage.

100 g per hour of sodium hydroxide solution are fed into the quenching circuit in the form of a 20% strength aqueous solution.

The crude reaction product is fed directly, without further treatment, to the Diels-Alder reaction with butadiene. The reactor used is a 3-chamber stirred kettle with a down-stream delay tube which is heated to temperatures of 120° C. Butadiene is added in excess, in a quantity of 12 kg/hour. The reaction is carried out under a pressure of 20 bars and with a residence time of approximately 90 minutes. After the reaction, the product is let down into a container, the greater part of the excess butadiene flashing. This butadiene is again compressed to 20 bars by means of a compressor and is recycled into the Diels-Alder reactor, the quantity of butadiene which has been consumed being replaced.

The product from the Diels-Alder reactor is fed without further treatment to the third reaction stage, the oxy-dehydrogenation of tetrahydroanthraquinone to give anthraquinone. The quantity is approximately 75 kg/hour and the product contains 12% by weight of tetrahydroanthraquinone and 7.5% by weight of phthalic anhydride, besides small quantities of impurities and a large quantity of excess naphthalene. The oxy-dehydrogenation reactor is constructed in the form of a rectifying column, The column has a diameter of 300 mm and a height of 8.7 m. In the stripping section the column is equipped with valve trays. The feed product is introduced at the sump. The sump is constructed in the form of a 2-kettle cascade, placed one on top of the other.

Approximately a further 12 kg/hour of phthalic anhydride from the downstream column, for separating phthalic anhydride and anthraquinone, are additionally recycled into the stripping section. 70 Standard cubic meters per hour of the abovementioned circulation gas are passed into the sump of the column. The composition is about 4.0% by volume of oxygen and 0.5% by volume of naphthalene besides the abovementioned inert gaseous constituents.

The column is operated under the system pressure of 6.5 bars and has a sump temperature of 180° C. in the lower kettle and of 200° C. in the upper kettle. The oxy-dehydrogenation of tetrahydroanthraquinone takes place virtually quantitively.

Approximately 70 kg/hour of crude product are withdrawn from the upper kettle of the 2-kettle cascade. This product contains approximately 12% by weight of anthraquinone, 50% by weight of naphthalene, approximately 1.5% by weight of higher-boiling residues and approximately 1% by weight of unknown by-products. The difference from 100 arises from the content of phthalic anhydride.

In a downstream column, at a pressure of 120 mbars, the reaction product is largely freed from naphthalene, which is added again, in the gaseous state, via a vaporiser to the circulation gas upstream of the naphthalene oxidation.

In order to separate crude phthalic anhydride as a top product and crude anthraquinone as a bottom product, the reaction mixture is fed into a rectifying column which is operated at 250 mbars. The column is designed in a customary manner as a packed column. Because of the high temperature required, the sump is heated electrically. The sump temperature is 310° C. Crude phthalic anhydride is withdrawn at the top of the column. The quantity of phthalic anhydride taken off is approximately 17 kg/hour. As explained above, approximately 12 kg/hour of this are pumped back into the system in which tetrahydroanthraquinone is oxy-dehydrogenated. The product obtained at the sump of the column contains about 8 kg/hour of anthraquinone and approximately 1.5 kg/hour of higher-boiling by-products. The ratio of anthraquinone to higher-boiling by-products is therefore approximately 1:0.19. This sump product is fed to a conventional thin film evaporator. A discharge screw equipped with cooling is fitted to give trouble-free discharge of the higher-boiling by-products. The higher-boiling products are obtained in a solid or liquid form and are removed from the process. Residual anthraquinone is obtained from the mixture which has been removed by sublimation or extraction with xylene and subsequent crystallisation. The thin film evaporator is operated under normal pressure and the anthraquinone vaporises and is withdrawn in the form of a gas. The apparatus is electrically heated in order to reach the high temperatures of about 450° C. A rectifying attachment, 1 m long and filled with packing, is fitted above the thin film evaporator. Anthraquinone is purified under reflux in this and leaves the system at first in a liquid state and is crystallised in a cooled screw conveyor on the outlet side and discharged.

The crude phthalic anhydride which is produced as a by-product is now freed from residues of entrained impurities. The crude phthalic anhydride is fed to a column of conventional design. The column is operated at a pressure of 150 mm Hg. Unidentified low-boiling impurities are withdrawn via the head of this column and are recycled into the process upstream of the Diels-Alder reaction. The sump product of this column, which, besides phthalic anhydride, contains a small quantity of unknown by-products, is fed to a further column in which the greater part of the phthalic anhydride is taken off as a top product. This phthalic anhydride is now colourless.

A quantity of approximately 1 kg per hour of crude phthalic anhydride is withdrawn at the sump of the column and is recycled to the column for the oxy-dehydrogenation of tetrahydroanthraquinone.

EXAMPLE 2

The procedure followed is as in Example 1, but, instead of the aqueous solution of sodium hydroxide, a stoichiometrically equivalent quantity of ammonia in the form of an aqueous solution is added. Virtually the same result as in Example 1 is obtained.

EXAMPLE 3 (Comparison example)

The reaction is carried out as in Example 1, but without adding sodium hydroxide solution.

The ratio of anthraquinone to higher-boiling by-products in the sump of the column for separating phthalic anhydride from anthraquinone and higher-boiling by-products is 1:0.4.

In the oxidation of naphthalene, 15% of the naphthalene reacted is converted into carbon dioxide.

What is claimed is:

1. In a process for the preparation of anthraquinone by catalytic oxidation of naphthalene in the gas phase to provide a reaction product, obtained by quenching, cooling or quenching and cooling, containing naphthaquinone and phthalic anhydride, treating said reaction product directly with butadiene to provide tetrahydroanthraquinone, oxidation by means of molecular oxygen of the tetrahydroanthraquinone contained in this reaction product, to give anthraquinone, and separation of naphthalene, phthalic anhydride, anthraquinone and by-products by distillation, the gases produced in the quenching, cooling, or quenching and cooling of the gases from the naphthalene oxidation and the gases from the oxidation of the tetrahydroanthraquinone to give anthraquinone being completely or partially recycled to the oxidation of naphthalene, characterized in that compounds with an alkaline reaction are introduced in an amount of 0.001 to 0.1% by weight relative to the naphthalene converted in the naphthalene oxidation between the naphthalene oxidation and the reaction with butadiene, or into the gas streams which are recycled to the oxidation of naphthalene.

2. Process according to claim 1, characterized in that the compounds with an alkaline reaction are added shortly before or at the entry of the gases from the naphthalene oxidation into the quenching, cooling, or quenching and cooling device or to the liquid phase in the quenching, cooling device.

3. Process according to claim 1, characterized in that alkali metal or alkaline earth metal compounds, ammonia, organic bases or mixtures thereof are employed as the compounds with an alkaline reaction.

4. Process according to claim 1, characterized in that alkali metal or alkaline earth metal oxides, hydroxides, carbonates, bicarbonates or salts of organic acid or mixtures thereof are employed.

5. Process according to claim 1, characterized in that sodium hydroxide, potassium hydroxide, calcium carbonate or ammonia is employed as the compound with an alkaline reaction.

6. Process according to claim 1, characterized in that the compounds with an alkaline reaction are added in a gaseous, liquid or solid form.

7. Process according to claim 1, characterized in that the compounds with an alkaline reaction are added as a mixture with solvents or diluents.

8. Process according to claim 1, characterized in that the compounds with an alkaline reaction are employed in an amount of 0.005 to 0.01% by weight, relative to the naphthalene converted in the naphthalene oxidation.

* * * * *